(12) United States Patent
Sumiya

(10) Patent No.: US 7,281,796 B2
(45) Date of Patent: Oct. 16, 2007

(54) OPHTHALMIC APPARATUS

(75) Inventor: Toshifumi Sumiya, Nukata-gun (JP)

(73) Assignee: Nidek Co., Ltd., Gamagori (JP)

( * ) Notice: Subject to any disclaimer, the term of this patent is extended or adjusted under 35 U.S.C. 154(b) by 472 days.

(21) Appl. No.: 10/902,113

(22) Filed: Jul. 30, 2004

(65) Prior Publication Data

US 2005/0030474 A1    Feb. 10, 2005

(30) Foreign Application Priority Data

Aug. 4, 2003    (JP)    ............... 2003-286177

(51) Int. Cl.
*A61B 3/10*    (2006.01)
(52) U.S. Cl. ..................... 351/205; 351/211
(58) Field of Classification Search ........ 351/200–208, 351/221–223, 243
See application file for complete search history.

(56) References Cited

U.S. PATENT DOCUMENTS

| | | | |
|---|---|---|---|
| 5,270,749 A | * | 12/1993 | Okumura .................... 351/211 |
| 5,341,180 A | * | 8/1994 | Isogai et al. ................ 351/206 |
| 5,777,719 A | | 7/1998 | Williams et al. ............. 351/212 |
| 6,042,233 A | | 3/2000 | Mihashi et al. .............. 351/221 |
| 6,273,566 B1 | | 8/2001 | Kobayashi et al. .......... 351/221 |

FOREIGN PATENT DOCUMENTS

EP    1 393 700 A1    3/2004

* cited by examiner

*Primary Examiner*—M. Hasan
(74) *Attorney, Agent, or Firm*—Oliff & Berridge, PLC

(57) ABSTRACT

An ophthalmic apparatus which allows a patient to experience a manner of view after surgery (after correction) prior to surgery (prior to correction) and is capable of obtaining information required for performing refractive surgery suitable for the patient. The apparatus, which allows a patient to experience a manner of view after correction of optical aberration of a patient's eye, includes a target presenting optical system for presenting a target which the patient's eye is made to visually recognize, an aberration correcting optical system, which is arranged within an optical path of the target presenting optical system and has a light shaping optical unit which performs light shaping, for correcting the optical aberration of the patient's eye, an input unit which inputs data for correcting the optical aberration of the patient's eye, and a control unit which controls driving of the aberration correcting optical system based on the inputted correction data.

6 Claims, 3 Drawing Sheets

OPHTHALMIC APPARATUS

BACKGROUND OF THE INVENTION

1. Field of the Invention

The present invention relates to an ophthalmic apparatus which allows a patient to experience a manner of view after surgery (after correction) prior to refractive surgery to change a corneal shape.

2. Description of Related Art

Conventionally, when ametropia (refractive error) of an eye is corrected, spectacles or contact lenses have been used. For the same purpose, recently, refractive surgery is increasingly performed for ablating a cornea with a laser beam to change a corneal shape. In most recent times, a method is proposed where wavefront aberration of an eyeball is measured and an ablation amount is determined based on a result of the measurement so as to correct even higher order aberration of an optical system of the eyeball by ablating the cornea based on the determined ablation amount.

However, in the refractive correction by changing the corneal shape, different from the refractive correction with the spectacles or contact lenses, a patient cannot confirm a manner of view after correction until posterior to surgery. Therefore, the patient Sometimes feels anxiety about or perceives a gap about the manner of view after surgery (after correction). Further, since the manner of view after surgery (after correction) which the patient prefers is different according to his/her own circumstances (a lifestyle, a working environment, and the like), it is not simply proper to perform correction such that an object forms an image at one point on a retina. For example, in a case where an accommodation function of the eye is lowered due to presbyopia, if correction is made such that an object at a long (far) distance forms an image at one point on the retina while eliminating the higher order aberration, there may be cases where an object at a short (near) distance becomes difficult to see and visual acuity at a distance in daily needs is insufficiently obtained.

SUMMARY OF THE INVENTION

An object of the invention is to overcome the problems described above and to provide an ophthalmic apparatus which allows a patient to experience a manner of view after surgery (after correction) prior to surgery (prior to correction) and is capable of obtaining information required for performing refractive surgery suitable for the patient.

To achieve the objects and in accordance with the purpose of the present invention, an ophthalmic apparatus has a target presenting optical system for presenting a target which the patient's eye is made to visually recognize, an aberration correcting optical system, which is arranged within an optical path of the target presenting optical system and has a light shaping optical unit which performs light shaping, for correcting the optical aberration of the patient's eye, an input unit which inputs data for correcting the optical aberration of the patient's eye, and a control unit which controls driving of the aberration correcting optical system based on the inputted correction data.

Additional objects and advantages of the invention are set forth in the description which follows, are obvious from the description, or may be learned by practicing the invention. The objects and advantages of the invention may be realized and attained by the ophthalmic apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
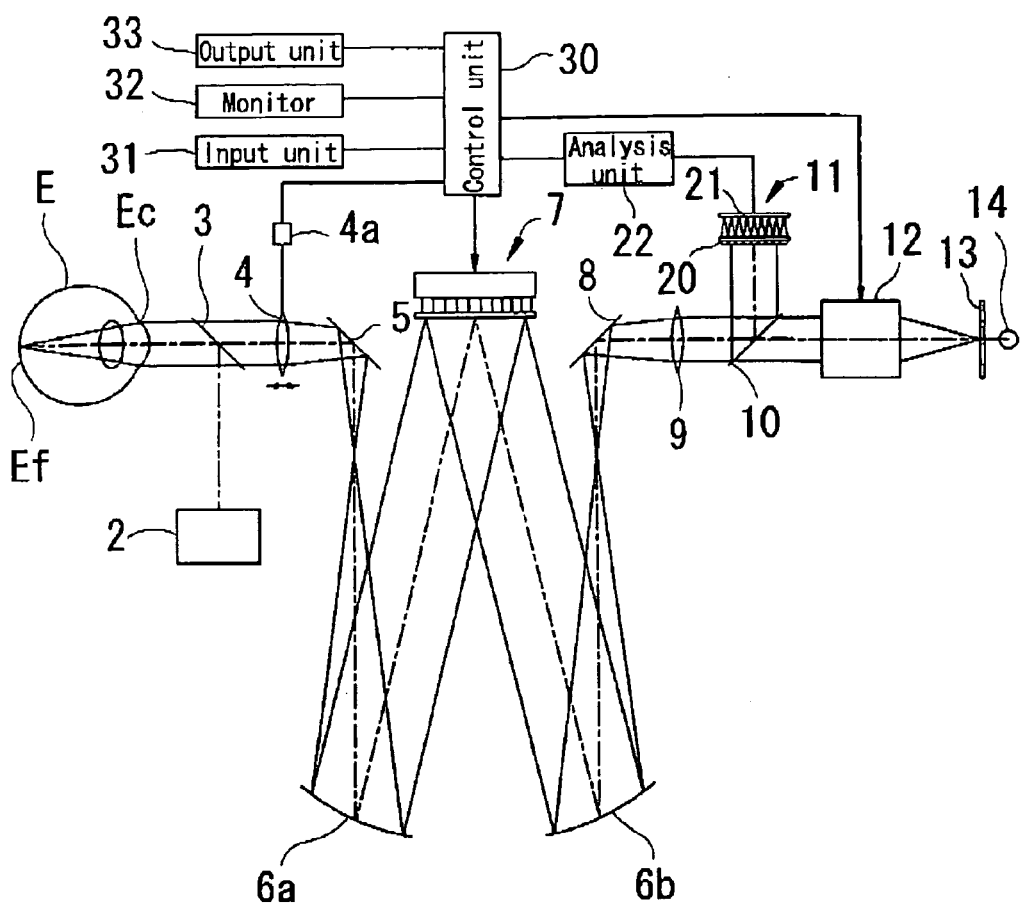
FIG. 1 is a view showing a schematic configuration of an optical system in an ophthalmic apparatus consistent with the present invention.

A detailed description of one preferred embodiment of an ophthalmic apparatus embodied by the present invention is provided below with reference to the accompanying drawings. FIG. 1 is a view showing a schematic configuration of an optical system in an ophthalmic apparatus consistent with the present invention. The optical system is broadly divided into an aberration measuring optical system, an aberration correcting optical system, and a target presenting optical system.

First, the aberration measuring optical system and the aberration correcting optical system are described. A light source 2, which is constituted of an SLD (Super Luminescent Diode), an LD (Laser Diode), or the like, emits a thin beam of infrared light. An infrared half mirror 3, having properties of reflecting a part of infrared light and transmitting a part thereof as well as transmitting nearly a whole part of visible light, reflects a part of the infrared light emitted from the light source 2 toward a patient's eye E and transmits a part of the infrared reflection light from the eye E. A parabolic mirror 6a, having a reflecting surface parabolically curved, reflects the infrared reflection light, which is collected by a lens 4 via a plane mirror 5, toward a deformable mirror 7 as a parallel light bundle (flux).

Figure 2:
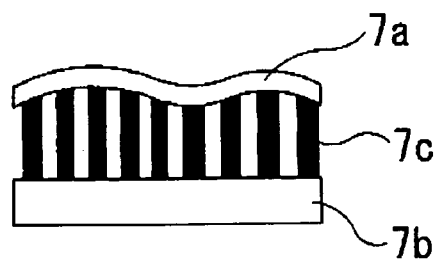
FIG. 2 is a view showing a schematic configuration of a deformable mirror.

The deformable mirror 7 having a deformable reflecting surface can change locally a reflecting direction of light. As shown in FIG. 2, the deformable mirror 7 includes a deformable mirror surface 7a in a membrane shape which reflects incident light, abase part 7b, and a plurality of piezo-elements 7c sandwiched between the mirror surface 7a and the base part 7b. The piezo-elements 7c are configured as a two-dimensional array on the base part 7b. And, the piezo-elements 7c are selectively applied voltage to deform the mirror surface 7a. Besides, the deformable mirror 7 is also used for light shaping for correcting optical aberration of the eye E at the time of target presentation to the eye E by the target presenting optical system described later.

Meanwhile, a DMD (Digital Micromirror Device) may be used for the light shaping for correcting the optical aberration of the patient's eye. In the DMD, a plurality of small mirrors, of which a reflection angle is variable, are configured as a two-dimensional array, and each reflection angle is controlled to change locally the reflecting direction of the light.

In addition, a PPM (Programmable Phase Modulator) may also be used for the light shaping for correcting the optical aberration of the patient's eye. The PPM is prepared by coupling an optically-addressed phase modulator PAL-SLM (Parallel Aligned Nematic Liquid Crystal Spatial Light Modulator) with an electrically-addressed intensity modulator LCD (Liquid Crystal Display) using an optical image transmitting element (an FOP (Fiber optic Plate) or a lens), and also incorporating a write-in laser.

Figure 3:
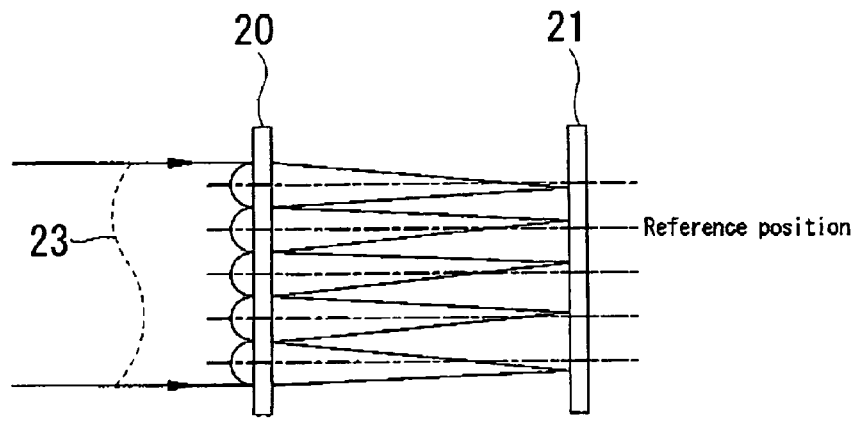
FIG. 3 is a view showing a schematic configuration of a Hartmann-Shack wavefront sensor.

A parabolic mirror 6b, having a reflecting surface parabolically curved, collects the infrared reflection light reflected by the deformable mirror 7 and makes it enter a wavefront sensor 11 via a plane mirror 8, a condenser lens 9, and a dichroic mirror 10. The dichroic mirror 10 has properties of reflecting infrared light and transmitting visible light. The wavefront sensor 11 is a Hartmann-Shack wavefront sensor, and includes, as shown in FIG. 3, a lens array 20 in which microlenses are configured as a two-dimensional lattice array, and a CCD camera 21 which is arranged at a focal surface of each microlens. The lens array 20 is arranged in a position approximately conjugate with a pupil of the eye E.

The light source 2 to the wavefront sensor 11 which are mentioned above constitute the aberration measuring optical system, and the infrared half mirror 3 to the dichroic mirror 10 among them constitute the aberration correcting optical system.

Next, the target presenting optical system will be described. A lens optical system 12 is capable of optically changing a distance between a target of a target plate 13 illuminated by an illumination lamp (a light source) 14 which emits visible light and the eye E using a zoom lens or the like, and presenting to the eye E the target at different distances for visual recognition such as a long (far) distance and a short (near) distance. As for the target of the target plate 13, various ones may be used such as a visual acuity chart having Landolt rings, numerics and the like, and scenic views. The illumination lamp 14 to the infrared half mirror 3 constitute the target presenting optical system. On a target presenting optical path between the lens optical system 12 and the eye E, the aberration correcting optical system constituted of the half mirror 3 to the dichroic mirror 10 as mentioned above is arranged.

Incidentally, the target presenting optical system is also employed as a fixation target presenting optical system at which the patient is made to fixate at the time of measuring wavefront aberration, and is capable of fogging by actuating the lens optical system 12.

A control unit 30 controls driving of the deformable mirror 7, the lens optical system 12, and the like. An analysis unit 22 performs analysis for obtaining the wavefront aberration of the eye E based on an output signal from the wavefront sensor 11. Analysis results obtained by the analysis unit 22 (data on an amount of the wavefront aberration) are inputted to the control unit 30. Further, an input unit 31, a monitor 32, and an output unit 33 are connected to the control unit 30. The input unit 31 is used as means for inputting an instruction signal for adjusting a correction amount of the wavefront aberration or means for inputting an instruction signal for changing the distance to present the target. The monitor 32 displays information inputted from the analysis unit 22 and the input unit 31.

Next, the measurement of the wavefront aberration of the eye E will be described. The infrared light emitted from the light source 2 is reflected by the infrared half mirror 3 to be directed into the eye E, and is collected at one point on a fundus Ef to form a point image. The infrared light scattered and reflected by the fundus Ef is transmitted through the infrared half mirror 3 and is converged by the lens 4 and once collected there.

If the eye E does not have aberration, the infrared reflection light reflected by the mirror 5 is made a parallel light bundle (flux) by the parabolic mirror 6a and is reflected by the deformable mirror 7. Besides, at the time of measuring the wavefront aberration, the mirror surface 7a of the deformable mirror 7 is made in a plane state having no inequalities or inclination. The infrared reflection light reflected by the deformable mirror 7 is reflected by the parabolic mirror 6b to be collected again and then diffused, and is reflected by the mirror 8 and then is made again a parallel light bundle (flux) by the lens 9. The infrared reflection light transmitted through the lens 9 is reflected by the dichroic mirror 10 and enters the wavefront sensor 11.

If the eye E has aberration, the infrared reflection light entering the wavefront sensor 11 has a wave front 23 (see FIG. 3) affected by the aberration. When the infrared reflection light has a distorted wave front, it enters the CCD camera 21 as an inclined light bundle (flux) through the respective microlenses. The inclination of the light bundle appears as positional deviation of point images on the CCD camera 21. The positional deviation of the point images is obtained using reference positions (indicated by alternate long and short dashed lines in FIG. 3) which are determined when a non-aberration optical system is measured. And, the inclination of the wave front passed through the microlenses is obtained from the positional deviation of the point images, and the total wavefront aberration is obtained from data on the wave front.

Refractive power of the eye E is also obtained from the analysis results of the wavefront aberration. If a far point of the eye E is measured, based on the once obtained refractive power, the target plate 13 (target) and the fundus Ef are placed at approximately conjugate positions using the lens optical system 12, and then fogging is made by an appropriate diopter. By the fogging, the wavefront aberration is measured again by the wavefront sensor 11 in a state where accommodation power of the eye E is relieved.

In addition, if a main operative distance of the patient is the short distance, the target is presented at this operative distance, and the wavefront aberration is measured in a state where the eye E is applied an accommodative load, so that the amount of the wavefront aberration to be corrected is obtained in agreement with the operative distance.

Next, a description is given on a method for providing an experience of a manner of view after correction of the wavefront aberration of the eye E. For the wavefront aberration correction, the deformable mirror 7 is used. Measurement data on the wavefront aberration is inputted from the analysis unit 22 to the control unit 30. In a case where the eye E is corrected to be in a non-aberration state, the measured wavefront aberration is regarded as the correction amount. The control unit 30 calculates a corrective deformation amount of the deformable mirror 7 so as to make the inputted wavefront aberration to be zero. The control unit 30 applies voltage to the piezo-elements 7c to deform the mirror surface 7a of the deformable mirror 7 by the deformation amount. Then, the illumination lamp 14 is lit, and the target is presented to the eye E via the aberration correcting optical system including the deformable mirror 7. Visible target light is transmitted through the lens optical system 12, the dichroic mirror 10, the lens 9, the mirror 8, the parabolic mirror 6b, the deformable mirror 7 being deformed so as to correct the wavefront aberration, the parabolic mirror 6a, the mirror 5, the lens 4, and the half mirror 3 to head for the fundus Ef. The deformable mirror 7 can change locally the reflecting direction of the light; therefore, high order aberration other than a spherical component (a defocus component) and an astigmatic component is corrected. The eye E can thereby experience the manner of view in a case where the wavefront aberration of the eyeball is corrected to be zero. If the target is a visual acuity target, the eye E may experience to what degree of visual acuity the target can be seen.

At this time, the lens optical system 12 is driven to change with complete control an optical distance between the eye E and the target in a range from a far-vision (far-sight) distance to a near-vision (near-sight) distance with respect to the eye E, so that the patient can experience the manner of view after correction of the wavefront aberration at different distances. Therefore, the manner of view after refractive surgery performed by the correction amount of the wavefront aberration as above can be previously recognized. The lens optical system 12 is driven and controlled by the control unit 30 according to the instruction signal from the input unit 31.

Figure 4:
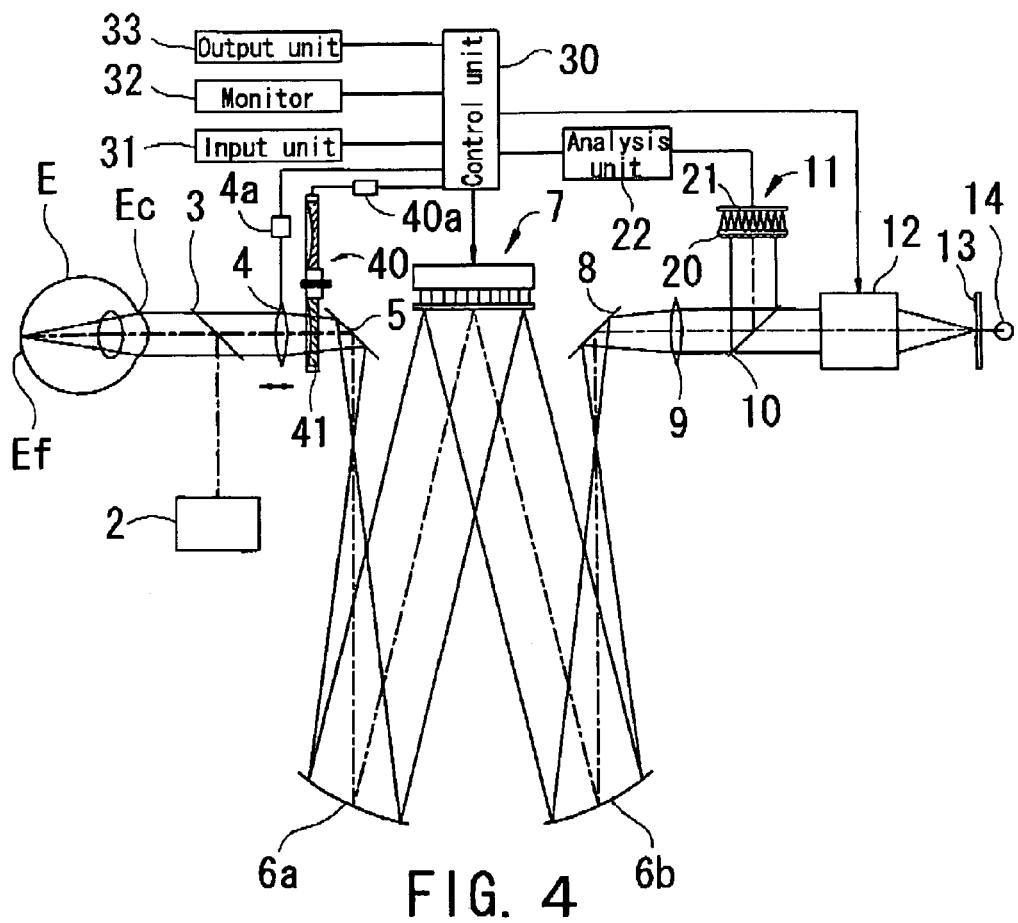
FIG. 4 is a view showing a schematic configuration of the optical system in the ophthalmic apparatus in which a spherical and cylindrical component correcting optical system is provided in addition to the deformable mirror.

Besides, for accommodating a case where ametropia (refractive error) of the spherical component and the cylindrical component of the eye E is seriously great (i.e., a case where ametropia exceeds a correction range of the deformable mirror 7), it is preferable to provide an optical system for correcting the spherical component and the cylindrical component aside from the deformable mirror 7. For example, as shown in FIG. 4, the correction optical system for the spherical component is constituted such that the lens 4 (or the lens 9) is moved in its optical axis direction by a moving device 4a. The correction optical system for the cylindrical component is constituted of a plurality of cylindrical lenses 41 with different power, and a lens disk 40 having openings. The cylindrical lenses 41 are configured to be rotatable about their optical axes when the cylindrical component requires correction, the lens disk 40 is rotated by a rotating device 40a to arrange the cylindrical lenses 41 with corrective power on an optical axis of the target presenting optical system (on an optical axis of the lens 4), and the cylindrical lenses 41 are rotated in accordance with an astigmatic axial angle.

Further, through the experience of the manner of view at far vision and near vision while changing a residual amount of the wavefront aberration, in other words, the correction amount of the wavefront aberration of the patient's eye, a correction amount suitable for the patient may be determined. Especially, regarding the patient for whom near vision has become difficult since an accommodation function of the eye is outstandingly lowered due to presbyopia, the manner of view of appropriate quality for the patient can be provided by leaving the wavefront aberration to the eyeball according to the lifestyle of the patient. In this case, the correction amount of the wavefront aberration is adjusted using the input unit 31. As a method for adjusting the correction amount, for example, in the Zernike's polynomial used in wavefront analysis, an aberration component is divided by each order, and the residual wavefront aberration amount for each order is adjusted. The control unit 30 controls to move the deformable mirror 7 in accordance with data on the adjustment, and form the aberration correcting optical system into a state where the wavefront aberration of the eye E is left. The patient is made to visually recognize the target via the aberration correcting optical system. Made to experience the manner of view of the target at near vision and far vision while changing the residual wavefront aberration amount, the patient can subjectively confirm the manner of view which the patient him/herself prefers. The correction amount suitable for the patient may be thereby determined.

Figure 5:
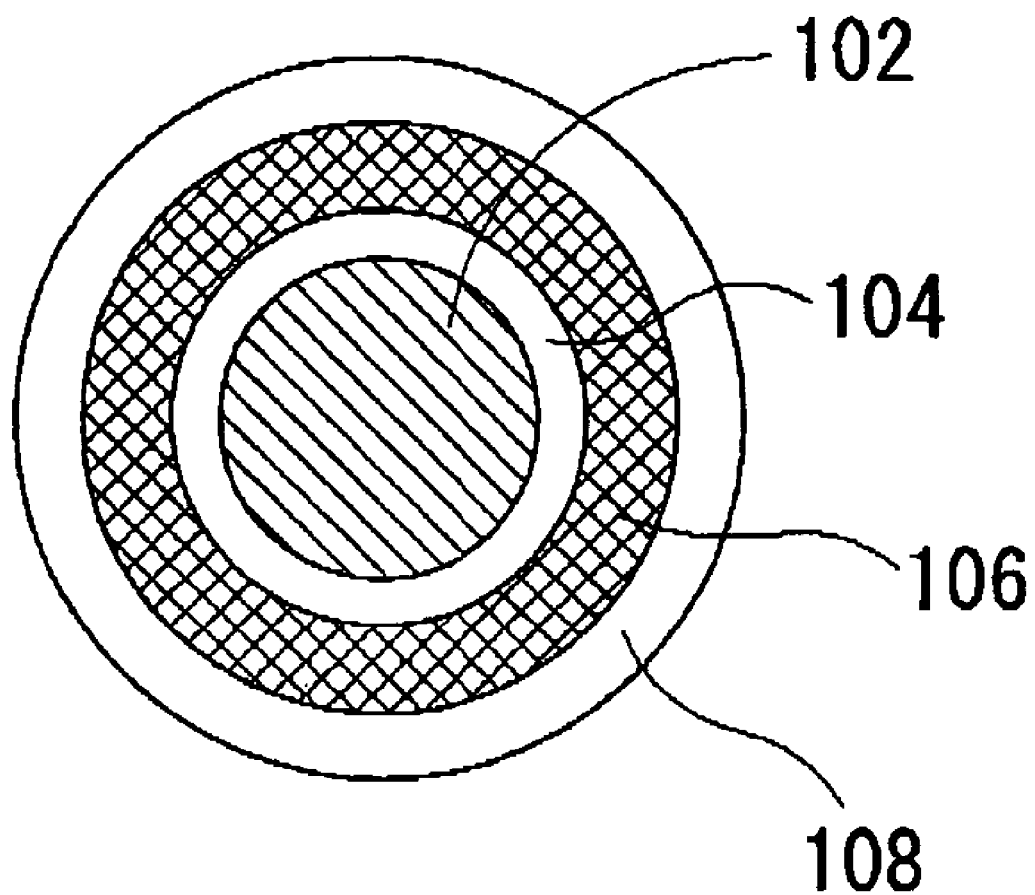
FIG. 5 is a view illustrating a correction pattern when a far-vision (far-sight) zone and its correction amount, and a near-vision (near-sight) zone and its correction amount are established.

Additionally, if the patient's eye is presbyopia, it is also possible that correction data including a far-vision zone and its correction amount, and a near-vision zone and its correction amount is inputted through the input unit 31 for the experience of the manner of view after correction. For example, as shown in FIG. 5, a far-vision zone 102 is configured at the center, and an annular near-vision zone 106 is configured outside the far-vision zone 102, and then their respective correction amounts are established. Provided between the far-vision zone 102 and the near-vision zone 106 is an intermediate-vision zone 104 where the correction amount changes progressively. Provided outside the near-vision zone 106 is a transition zone 108. Besides, the far-vision zone 102 and the near-vision zone 106 may be conversely arranged. The control unit 30 calculates the deformation amount of the deformable mirror 7 from data on this correction pattern, and makes the mirror surface 7a deform by the deformation amount through driving the piezo-elements 7c. Then, the target 13 is changed to be in the far-vision distance and the near-vision distance, and the patient is made to experience the manner of view thereof. In addition, sizes of the far-vision zone 102 and the near-vision zone 106, and the respective correction amounts are adjusted for the experience of the manner of view. Thereby, the correction amount suitable for the patient is determined.

The data on the correction amount determined subjectively by the patient as mentioned above is outputted from the output unit 33 via electronic recording media or a communication cable to a computer for calculating data on a corneal ablation amount or a corneal surgery apparatus for performing refractive surgery by a laser beam. At the time of refractive surgery, the corneal ablation amount is determined based on the outputted correction amount.

In the ophthalmic apparatus consistent with the preferred embodiment as described above, the wavefront aberration measuring optical system having the light source 2, the wavefront sensor 11, and the like is incorporated; however, another apparatus may be used instead. In this case, an external wavefront aberration measuring apparatus may previously obtain the data on the wavefront aberration, and this data may be inputted from the input unit 31.

Further, another constitution may be employed where a target of an external apparatus is used as the target in the target presenting optical system, and only the aberration correcting optical system is arranged on an optical path to present the target. In this case, a known visual acuity chart, a space-saver target presenting apparatus or the like may be used to present the target at which the patient is made to visually recognize. In recognition for near vision, a near view chart or the like which is used in the visual acuity test may be used.

Incidentally, in the aforementioned preferred embodiment, in order to correct the optical aberration of the patient's eye, the measurement data on wavefront aberration distribution of the patient's eye is utilized; however, measurement data on eye refractive power distribution of the patient's eye may be also utilized. In the measurement of the wavefront aberration distribution and that of the eye refractive power distribution, the measurement results are different from each other in expressive form; however, they coincide with each other in the sense that optical aberration of the eye is measured in both the measurement. Since means for measuring the eye refractive power distribution of the patient's eye is described in EP 1393700A2 (WO 02/098335, Japanese Patent Application Unexamined Publication No. P2002-355219A) and other materials, please refer to them.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus which allows a patient to experience a manner of view after correction of optical aberration of a patient's eye, the apparatus comprising:
   a target presenting optical system for presenting a target which the patient's eye is made to visually recognize;
   an aberration correcting optical system, which is arranged within an optical path of the target presenting optical system and has a light shaping optical unit which performs light shaping, for correcting the optical aberration of the patient's eye, the light shaping optical unit locally changing a direction of a light bundle which is reflected from or passes through the light shaping optical unit by applying a voltage;
   an input unit which inputs measurement data of one of wavefront aberration distribution and eye refractive power distribution of the patient's eye as correction data for correcting the optical aberration including higher order aberration of the patient's eye; and
   a control unit which controls driving of the light shaping optical unit based on the inputted correction data.

2. The ophthalmic apparatus according to claim 1, further comprising a measuring optical system for measuring one of the wavefront aberration distribution and the eye refractive power distribution of the patient's eye,
   wherein the input unit inputs the obtained measurement data as the correction data.

3. The ophthalmic apparatus according to claim 1, wherein the input unit is capable of adjusting the correction data.

4. The ophthalmic apparatus according to claim 1, wherein the target presenting optical system is capable of changing a distance to present the target.

5. An ophthalmic apparatus which allows a patient to experience a manner of view after correction of optical aberration of a patient's eye, the apparatus comprising:
   a target presenting optical system for presenting a target which the patient's eye is made to visually recognize;
   an aberration correcting optical system, which is arranged within an optical path of the target presenting optical system and has a light shaping optical unit which performs light shaping, for correcting the optical aberration of the patient's eye;
   an input unit which inputs data for correcting the optical aberration of the patient's eye; and
   a control unit which controls driving of the aberration correcting optical system based on the inputted correction data,
   wherein the aberration correcting optical system has a spherical and cylindrical component correcting optical unit which corrects a spherical component and a cylindrical component.

6. An ophthalmic apparatus which allows a patient to experience a manner of view after correction of optical aberration of a patient's eye, the apparatus comprising:
   a target presenting optical system for presenting a target which the patient's eye is made to visually recognize;
   an aberration correcting optical system, which is arranged within an optical path of the target presenting optical system and has a light shaping optical unit which performs light shaping, for correcting the optical aberration of the patient's eye;
   an input unit which inputs data for correcting the optical aberration of the patient's eye; and
   a control unit which controls driving of the aberration correcting optical system based on the inputted correction data,
   wherein the input unit inputs data on a far-vision zone and data on a correction amount thereof, and data on a near-vision zone and data on a correction amount thereof as the correction data.

* * * * *